United States Patent
Deem et al.

(10) Patent No.: US 6,640,191 B1
(45) Date of Patent: Oct. 28, 2003

(54) LIBRARY DESIGN IN COMBINATORIAL CHEMISTRY BY MONTE CARLO METHODS

(75) Inventors: Michael W. Deem, Los Angeles, CA (US); Marco Falcioni, Santa Clara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/474,965

(22) Filed: Dec. 30, 1999

(51) Int. Cl.⁷ .................. G01N 33/48; G01N 31/00; G01N 33/566; G01N 33/543; G01N 33/536; C12Q 1/00; C12Q 1/68

(52) U.S. Cl. ............... 702/19; 702/27; 435/4; 435/6; 436/501; 436/518; 436/536

(58) Field of Search .............. 702/27, 19; 435/6, 435/4; 436/501, 536, 518

(56) References Cited

U.S. PATENT DOCUMENTS 5,854,992 A * 12/1998 Shakhnovich et al. ........ 702/27

OTHER PUBLICATIONS

Hassan, Moises, et al. (1996) "Optimization and Visualization of Molecular Diversity of Combinatorial Libraries" Molecular Diversity, Vol 2, No. 1–2, pp 64–74.*

Balkenhohl, F., von dem Bussche–Hünnefeld, Lansky, A & Zechel, C. Combinatorial Synthesis of Small Organic Molecules. Angew. Chem. Int. Ed. Engl. 35, 2288–2337 (1996).

Service, Robert F. High Speed Materials Design. Science 277, 474–475 (1997).

Singh, J., Ator, M.A., Jaeger, E.P., Allen, M.P., Whipple, D.A., Soloweij, J.E., Chowdhary, S., & Treasurywala, A.M. Application of Genetic Algorithms to Combinatorial Synthesis: A Computational Approach to Lead Identification and Lead Optimization. J. Am. Chem. Soc. 118, 1669–1676 (1996).

Weber, L., Wallbaum, S., Broger, C. & Gubernator, K. Optimization of the Biological Activity of Combinatorial Compound Libraries by a Genetic Algorithm. Angew. Chem. Int. Ed. Engl. 34, 2280–2282 (1995).

Akporiaye, D. E., Dahl, I.M., Karlsson, A. & Wendelbo, R. Combinatorial approach to the hydrothermal synthesis of zeolites. Angew. Chem. Int. Ed. 37, 609–611 (1998).

Briceño, G., Chang, H., Sun, X., Schultz, P. G. & Xiang, X.–D. A class of cobalt oxide magnetoresistance materials discovered with combinatorial synthesis. Science 270, 273–275 (1995).

Danielson, E., Devenney, M., Giaquinta, D. M., Golden, J. H., Haushalter, R. C., McFarland, E. W., Poojary, D. M., Reaves, C. M., Weinberg, W. H. & Wu, X. D. A rare–earth phosphor containing one–dimensional chains identified through combinatorial methods. Science 279, 837–839 (1988).

Danielson, E., Golden, J. H., McFarland, E. W., Reaves, C. M., Weinberg, W. H. & Wu, X. D. A combinatorial approach to the discovery and optimization of luminescent materials. Nature 389, 944–948 (1997).

McFarland, E. W. & Weinberg, W. H. Combinatorial approaches to materials design. TIBTECH 17, 107–115 (1999).

Reddington, E., Sapienza, A., Gurau, B., Viswanathan, R., Sarangapani, S., Smotkin, E. S. & Mallouk, T. E. Combinatorial electrochemistry: A highly parallel, optical screening method for discovery of better electrocatalysts. Science 280, 1735–1737 (1998).

van Dover, R. B., Schneemeyer, L. F. & Fleming, R. M. Discovery of a useful thin–film dielectric using a composition–spread approach. Nature 392, 162–164 (1998).

Weinberg, W. H., Jandeleit, B., Self, K. & Turner, H. Combinatorial methods in homogeneous and heterogeneous catalysis. Curr. Opin. Chem. Bio. 3, 104–110 (1998).

Wang, J., Yoo, Y., Gao, C., Takeuchi, L, Sun, X., Chang, H., Xiang, X.–D. & Schultz, P. G. Identification of a blue photoluminescent composite material from a combinatorial library. Science 279, 1712–1714 (1998).

Xiang, X.–D., Sun, X., Briceño, G., Lou, Y., Wang, K.–A., Chang, H., Wallace–Freedman, W. G., Chang, S.–W. & Schultz, P. G. A combinatorial approach to materials discovery. Science 268, 1738–1740 (1995).

Gilbertson, S. R. & Wang, X. The combinatorial synthesis of chiral phosphine ligands. Tetrahed. Lett. 37, 6475–6478 (1996).

Bratley, P., Fox, B. L. & Niederreiter, H. Algorithm–738–programs to generate Niederreiter's Low–Discrepancy Sequences. ACM Trans. Math. Software 20, 494–495 (1994).

Burger, M. T. & Still, W. C. Synthetic ionophores. encoded combinatorial libraries of cyclen–based receptors for Cu2+ and Co2+. J. Org. Chem. 60, 7382–7383 (1995).

Burgess, K., Lim, H.–J., Porte, A. M. & Sulikowski, G. A. New catalysts and conditions for a C–H insertion reaction identified by high throughput catalyst screening. Angew. Chem. Int. Ed. 357 220–222 (1996).

(List continued on next page.)

*Primary Examiner*—John S. Brusca
*Assistant Examiner*—Shubo Zhou
(74) *Attorney, Agent, or Firm*—Fulbright & Jaworski L.L.P.

(57) ABSTRACT

Methods for generating multiple rounds of combinatorial libraries, which use Monte Carlo methods to search the multi-dimensional composition and non-composition space of variables in combinatorial chemistry; the combinatorial libraries generated and screened by such Monte Carlo methods; and an apparatus for generating and screening such libraries robotically. The process involves preparing a first set of samples, then changing the composition and non-composition variables of the samples using Monte Carlo sampling methods, and accepting proposed new samples according to a detailed balance acceptance criterion.

17 Claims, 3 Drawing Sheets

OTHER PUBLICATIONS

Cole, B. M., Shimizu, K. D., Krueger, C. A., Harrity, J. P. A., Snapper, M. L. Hoveyda, A. H. Discovery of chiral catalysts through ligand diversity: Ti–catalyzed enantioselective addition of TMSCN to meso epoxides. Angew. Chem. Int. Ed. 35, 1668–1671 (1996).

Cong, P., Doolen, R. D., Fan, Q., Giaquinta, D. M., Guan, S., McFarland, E. W., Poojary, D. M., Self, K., Turber, H. W. & Weinberg, W. H. High–throughput synthesis and screening of combinatorial heterogeous catalyst libraries. Angew. Chem. Int. Ed. 38, 484–488 (1999).

Dickinson, T. A. & Walt, D. R. Generating sensor diveristy through combinatorial polymer synthesis. Anal. Chem. 69, 3413–3418 (1997).

Falcioni, M. & Deem, M. W. A. biased Monte Carlo scheme for zeolite structure solution. J. Chem. Phys. 111, 1754–1766 (1999).

Francis, M. B., Jamison, T. F. & Jacobsen, E. N. Combinatorial libraries of transition–metal complexes, catalysts and materials. Curr. Opin. Chem. Biol. 2, 422–428 (1998).

Geyer, C.J. Markov chain Monte Carlo maximum likelihood in Computing Science and Statistics: Proceedings of the 23rd Symposium on the Interface 156–163 (American Statistical Association, New York, 1991.

Helmkamp, M. M. & Davis, M. E. Synthesis of porous silicates. Ann. Rev. Mater. Sci. 25, 161–192 (1995).

Liu, G. & Ellman, J. A. A general solid–phase synthesis strategy for the preparation of 2–pyrrolidinemethanol ligands. J. Org. Chem. 60, 7712–7713 (1995).

Marinari, E., Paxisi, G. & Ruiz–Lorenzo, J. Numerical simulations of spin glass systems in Spin Glasses and Random Fields (ed. Young, A.) vol. 12 of Directions in Condensed Matter Physics (World Scientific, Singapore, 1998).

Menger, F. M., Eliseev, A. V. & Mugulin, V. A. Phosphatase catalysis develped via combinatorial organic chemistry, J. Org. Chem. 60, 6666–6667 (1995).

Novet, T., Johnson, D. C. & Fister, L. Interfaces, interfacial reactions and superlattice reactants. Adv. Chem. Ser. 245, 425–469 (1995).

Pirrung, M. C. Spatially addressable combinatorial libraries. Chem. Rev. 97, 473–488 (1997).

Zones, S. I., Nakagawa, Y., Lee, G. S., Chen, C. Y. & Yuen, L. T. Searching for new high silica zeolites through a synergy of organic templates and novel inorganic conditions. Micropor. Mesopor. Mat. 21, 199–211 (1998).

\* cited by examiner

LIBRARY DESIGN IN COMBINATORIAL CHEMISTRY BY MONTE CARLO METHODS

This invention was made with Government support under Grant No. CTS-9702403, awarded by the National Science Foundation. The Government has certain rights in this invention.

BACKGROUND OF THE INVENTION

The goal of combinatorial materials discovery is to find compositions of matter that maximize a specific material property, such as superconductivity, magnetoresistance, luminescence, ligand specificity, sensor response, or catalytic activity. (See, e.g., McFarland, E. W. & Weinberg, W. H. Combinatorial approaches to materials design. TIBTECH 17, 107–115 (1999); Pirrung, M. C. Spatially addressable combinatorial libraries. Chem. Rev. 97, 473–488 (1997); Weinberg, W. H., Jandeleit, B., Self, K. & Turner, H. Combinatorial methods in homogeneous and heterogeneous catalysis. Curr. Opin. Chem. Bio. 3, 104–110 (1998); Xiang, X.-D., Sun, X., Briceno, G., Lou, Y., Wang, K.-A., Chang, H., Wallace-Freedman, W. G., Chang, S.-W. & Schultz, P. G. A combinatorial approach to materials discovery. Science 268, 1738–1740 (1995); Briceño, G., Chang, H., Sun, X., Schultz, P. G. & Xiang, X.-D. A class of cobalt oxide magnetoresistance materials discovered with combinatorial synthesis. Science 270, 273–275 (1995); Danielson, E., Golden, J. H., McFarland, E. W., Reaves, C. M., Weinberg, W. H. & Wu, X. D. A combinatorial approach to the discovery and optimization of luminescent materials. Nature 389, 944–948 (1997); Danielson, E., Devermey, M., Giaquinta, D. M., Golden, J. H., Haushalter, R. C., McFarland, E. W., Poojary, D. M., Reaves, C. M., Weinberg, W. H. & Wu, X. D. A rare-earth phosphor containing one-dimensional chains identified through combinatorial methods. Science 279, 837–839 (1988); Wang, J., Yoo, Y., Gao, C., Takeuchi, L, Sun, X., Chang, H., Xiang, X.-D. & Schultz, P. G. Identification of a blue photoluminescent composite material from a combinatorial library. Science 279, 1712–1714 (1998); Burger, M. T. & Still, W. C. Synthetic ionophores, encoded combinatorial libraries of cyclen-based receptors for $Cu^{2+}$ and $Co^{2+}$. J. Org. Chem. 60, 7382–7383 (1995); Liu, G. & Ellman, J. A. A general solid-phase synthesis strategy for the preparation of 2-pyrrolidinemethanol ligands. J. Org. Chem. 60, 7712–7713 (1995); Bilbertson, S. R. & Wang, X. The combinatorial synthesis of chiral phosphine ligands. Tetrahed. Lett. 37, 6475–6478 (1996); Francis, M. B., Jamison, T. F. & Jacobsen, E. N. Combinatorial libraries of transition-metal complexes, catalysts and materials. Curr. Opin. Chem. Biol. 2, 422–428 (1998); Dickinson, T. A. & Walt, D. R. Generating sensor diversity through combinatorial polymer synthesis. Anal. Chem. 69, 3413–3418 (1997); Menger, F. M., Eliseev, A. V. & Migulin, V. A. Phosphatase catalysis developed via combinatorial organic chemistry. J. Org. Chem. 60, 6666–6667 (1995); Burgess, K., Lim, H.-J., Porte, A. M. & Sulikowski, G. A. New catalysts and conditions for a C—H insertion reaction identified by high throughput catalyst screening. Angew. Chem. Int. Ed. 357 220–222 (1996); Cole, B. M., Shimizu, K. D., Krueger, C. A., Harrity, J. P. A., Snapper, M. L. Hoveyda, A. H. Discovery of chiral catalysts through ligand diversity: Ti-catalyzed enantioselective addition of TMSCN to meso epoxides. Angew. Chem. Int. Ed. 35, 1668–1671 (1996); Akporiaye, D. E., Dahl, I. M., Karlsson, A. & Wendelbo, R. Combinatorial approach to the hydrothermal synthesis of zeolites. Angew. Chem. Int. Ed. 37, 609–611 (1998); Reddington, E., Sapienza, A., Gurau, B., Viswanathan, R., Sarangapani, S., Smotkin, E. S. & Mallouk, T. E. Combinatorial electrochemistry: A highly parallel, optical screening method for discovery of better electrocatalysts. Science 280, 1735–1737 (1998); and Cong, P., Doolen, R. D., Fan, Q., Giaquinta, D. M., Guan, S., McFarland, E. W., Poojary, D. M., Self, K., Turber, H. W. & Weinberg, W. H. High-throughput synthesis and screening of combinatorial heterogeous catalyst libraries. Angew. Chem. Int. Ed. 38., 484–488 (1999)].

A variety of materials have been optimized or developed to date by combinatorial methods. Perhaps the first experiment to gather great attention was the demonstration that inorganic oxide high-$T_c$ superconductors could be identified by combinatorial methods (Xiang et al., supra). By searching several 128-member libraries of different inorganic oxide systems, the known compositions of superconducting BiSrCaCuO and YBaCuO were identified. Since then, many demonstrations of finding known materials and discoveries of new materials have appeared. Known compositions of magnetoresistant materials have been identified in libraries of various cobalt oxides (Briceño et al., supra). Blue and red phosphors have been identified from large libraries of 25,000 different inorganic oxides [Danielson et al. (1998), supra; Danielson et al. (1988), supra; and Wang et al., supra]. Polymer-based sensors for various organic vapors have been identified by combinatorial methods (Dickinson et al., supra). Catalysts for the oxidation of CO to $CO_2$ have been identified by searching ternary compounds of Pd, Pt, and Rh or Rh, Pd, and Cu (Pirrung, supra, and Cole et al., supra). Phase diagrams of zeolitic materials have been mapped out by a combinatorial "multiautoclave" (Akporiaye et al., supra). Novel enantioselective catalysts have been found by searching libraries of transition metal-peptide complexes (Cole et al., supra). Novel phosphatase catalysts were found by searching libraries of carboxylic acid-functionalized polyallylamime polymers (Menger et al., supra). New catalysts and conditions for C—H insertion have been found by screening of ligand-transition metal systems (Burgess et al., supra). A new catalyst for the conversion of methanol in a direct methanol fuel cell was identified by searching the quaternary composition space of Pt, Ir, Os, and Ru (Reddington et al., supra). Finally, a novel thin-film high dielectric compound that may be used in future generations of DRAM chips was identified by searching through over 30 multicomponent, ternary oxide systems [van Dover, R. B., Schneemeyer, L. F. & Fleming, R. M. Discovery of a useful thin-film dielectric using a composition-spread approach. Nature 392, 162–164 (1998)].

Present approaches to combinatorial library design and screening invariably amount to a grid search in composition space, followed by a "steepest-ascent" maximization of the figure of merit. Such optimization procedures, however, are inefficient methods at finding optima in high-dimensional spaces or when the figure of merit is not a smooth function of the variables. Indeed, the use of a grid search is what has limited essentially all current combinatorial chemistry experiments to quaternary compounds, i.e., to searching a space with three variables. What is needed is an automated, yet more efficient, procedure for searching composition space.

SUMMARY OF THE INVENTION

The present invention uses Monte Carlo methods to provide just such a powerful new procedure for searching a multi-dimensional space of variables in combinatorial chemistry. Moreover, the effectiveness of the new protocols is validated on the Random Phase Volume Model, showing the new methods to be superior to those in current practice.

The present invention provides a method for generating a combinatorial library, which begins by preparing a first set of current samples using a grid search or a random selection method. Preferably, each initial sample has at least one composition or non-composition variable selected by a random method. In one preferred Monte Carlo method, the first set of current samples is prepared by choosing the variables of each current sample at random from allowed values. Alternatively, the first set of current samples could be prepared by choosing the variables of each current sample via a quasi-random, low discrepancy sequence.

The next step is preparing a new set of proposed samples by changing the variables of each current sample by a Monte Carlo selection method. A preferred method for changing the variables is a random displacement protocol, which randomly changes at least one of the composition and non-composition variables of a randomly chosen current sample a small amount. The process continues until the variables of each sample of the set are changed. A swapping move, which trades a subset of the variables between at least one pair of randomly chosen current samples, may also be included in the protocol.

The present invention further provides a method of performing multiple rounds of generating the aforementioned combinatorial libraries, which includes the additional feedback steps of determining a figure of merit for each current and proposed sample and forming a modified set of current samples according to an acceptance criterion derived from a detailed balance condition. If the figure of merit of a proposed sample is greater than the figure of merit of the current sample, then the proposed sample is accepted and replaces the current sample. If the figure of merit of the proposed sample is less than the figure of merit of the current sample, the proposed sample will be accepted according to a predetermined probability.

In a preferred version of the method, the acceptance criterion following a random displacement is a probability determined by a detailed balance formula, which in this case is simply the Metropolis formula:

$$p=\min\{1, \exp[\beta(E_{proposed}-E_{current})]\}, \qquad (1)$$

wherein the parameter $\beta$ defines the scale of the variations of the figure of merit that are likely to be accepted, and E is the figure of merit.

In another preferred version of the method, the acceptance criterion of a swapping move, which swaps samples i and j in one subset is:

$$p=\min\{1, \exp\{\beta[E^i_{proposed}+E^j_{proposed}-E^i_{current}-E^j_{current}]\}. \qquad (2)$$

Parallel tempering is a more powerful method of the present invention for searching the space of composition and non-composition variables. In parallel tempering, the samples are grouped into two or more subsets. During the rounds of combinatorial chemistry each subset is updated using a different Metropolis probability, e.g. by using different values for the parameter $\beta$. The parallel tempering protocol includes an additional step of randomly exchanging two or more samples between the subsets. The exchange step is accepted with an acceptance criterion derived from a detailed balance condition.

The composition variables are preferably one or more mole fractions of an element or compound.

The non-composition variables can include film thickness, deposition method, guest composition, host composition, impurity level, temperature, pressure, pH, atmospheric composition, crystallinity, phase, morphology, method of nucleation, method of synthesis, and other processing variables.

The figure of merit typically measures a property, such as luminescence, catalytic activity or selectivity, superconductivity, giant or colossal magnetoresistance, dielectric screening, biological activity, binding affinity, or sensing ability.

The methods for generating and screening combinatorial libraries, outlined above, will typically be iterated for one or more rounds until a maximum figure of merit is obtained.

Other versions of the present invention include the combinatorial libraries generated according to the aforementioned protocols.

Yet another version of the present invention is directed to an apparatus for generating a combinatorial library. The apparatus typically includes: (a) one or more sample preparation robots to robotically prepare a first set of current samples and one or more new sets of proposed samples in accordance with a sample preparation protocol, whereby each sample has one or more variables that can be changed independently; (b) one or more analysis robots to robotically analyze each sample to determine a figure of merit; and (c) a robotic control device for generating a sample preparation protocol in accordance with the methods of the present invention.

The robotic control device will generally include: (1) a mechanism for selecting the variables to use in preparing the first set of current samples, wherein the variables are selected by either a grid search or a Monte Carlo method; and (2) a mechanism for selecting variables to use in preparing the new set of proposed samples, wherein the variables of each current sample are changed using a Monte Carlo selection method to give a proposed sample. In addition the device may include: (3) a mechanism for comparing the figure of merit of a proposed sample with the figure of merit of a current sample, wherein the variables of the current sample were changed to give the proposed sample; and (4) a mechanism for accepting a modified set of current samples, according to the detailed balance acceptance criterion, described above. In addition, the robotic control device may also include a mechanism to determine whether to continue with another round of proposed samples.

BRIEF DESCRIPTION OF THE DRAWINGS

These and other features, aspects, and advantages of the present invention will become better understood with regard to the following description, appended claims, and accompanying drawings, where:

DETAILED DESCRIPTION OF THE PREFERRED EMBODIMENTS

Combinatorial chemistry is an attempt to search a large compositional space for compounds with a high figure of merit. Exhaustive search is possible only for relatively small libraries of compositions. Grid searching is appropriate only in the case of a limited number of compositions and when the figure of merit changes smoothly with composition. We present here a search protocol inspired by methods from Monte Carlo simulation and suitable for large composition spaces and rough figure-of-merit landscapes.

In combinatorial chemistry, we search through the composition and non-composition variables to find good figure-of-merit values. The present invention concerns the combinatorial strategy wherein a library of N compositions of matter is made, and the desired property of each composition is measured. A new library is then constructed, and the process is repeated. We assume that the composition variables of each of the N compositions of matter can be varied independently of the other compositions of matter. Typically, the synthesis and screening would be under robotic control. Accordingly, the methods of the present invention provide an efficient protocol for controlling the robotic synthesis. We will consider both the solid-state case and the organic molecule case.

The term "Monte Carlo," as used herein, generally refers to any reasonably random or quasi-random procedure for generating values of allowed variables. Examples of Monte Carlo methods include choosing values: (a) randomly from allowed values; (b) via a quasi-random sequence like LDS (Low Discrepancy Sequence); (c) randomly, but biased with experimental or theoretical a priori information; and (d) from a non-trivial distribution via a Markov sequence.

More particularly, a "Monte Carlo" method is a technique which obtains a probabilistic approximation to the solution of a problem by using statistical sampling techniques. A preferred Monte Carlo method is a Markov process, i.e., a series of random events in which the probability of an occurrence of each event depends only on the immediately preceding outcome. Accordingly, a preferred MonteCarlo method of the present invention is a Markov process to sample any given probability distribution p. For any given value of the allowed variables, p is a non-negative function of the figure of merit measured experimentally. Typically p will increase monotonically with the figure of merit. The integral of p over all of the variables is one. (See Kalos, M. H. and Whitlock, P. A. "Monte Carlo Methods: Volume I: Basics," John Wiley & Sons, New York, 1986; and Frenkel, D., and Smit, B. "Understanding Molecular Simulation: From Algorithms to Applications,: Academic Press, San Diego, 1996).

As will be apparent to one of skill in the art, a variety of Markov procedures may be utilized in the Monte Carlo methods of the present invention. Examples of specific Markov procedures, described in further detail below, include a Metropolis algorithm, Metropolis with swapping, parallel tempering, and using a bias or an a priori probability.

I. What is Being Optimized

In combinatorial chemistry, we are attempting to find a material with a given property. We can formulate this question as an optimization problem: What is the composition that gives the best value for the given property? Alternatively, we can formulate the question as a sampling problem: Produce compositions from a given probability distribution, which depends on the given property. The property can be, for example, luminescence, catalytic activity or selectivity, superconductivity, giant or colossal magnetoresistance, dielectric screening, biological activity, binding affinity, or sensing ability. Typically, the given property is measured experimentally to provide a figure of merit.

II. What Are the Variables

Several variables can be manipulated in order to seek a material with an optimal figure of merit. Indeed, the methods of the present invention are particularly effective when there is a larger number of composition and non-composition variables. Preferably, at least four variables are manipulated, but there is no theoretical reason to restrict the number of variables to an absolute upper limit. As a practical matter, however, the time it takes to prepare a large number of samples and measure their figures of merit may limit the number of variables that can be tested. Accordingly, more preferred versions of the invention will keep the number of variables within a range that is consistent with such time limitations.

The composition variables of the present invention are certainly of prime importance. A composition variable is typically expressed as a relative value of a particular component in a multi-component mixture. For example, a composition variable may be characterized as a mole fraction of a particular substance having an allowed value of 0 to 1. Alternatively, a composition variable can be an atomic percent of a particular element having an allowed value of 0 to 100. Preferably, there are a plurality of composition variables.

The methods of the present invention can also include the manipulation of one or more non-composition variables. Preferably, there are fewer non-composition variables than composition variables. Typically, the non-composition variables will reflect additional processing conditions, such as temperature, pressure, pH, and atmospheric composition. Moreover, film thickness and deposition method can be non-composition variables for materials made in thin film form. [See, e.g., van Dover et al., supra; and Novet, T., Johnson, D. C. & Fister, L. Interfaces, interfacial reactions and superlattice reactants. *Adv. Chem. Ser.* 245, 425–469 (1995)]. Additional non-composition variables, such as guest composition, impurity level, and the "crystallinity" of the material, can also affect the figure of merit (Cong, et al, supra, and van Dover et al., supra). Methods of nucleation or synthesis, which may affect the phase or morphology of the material and so affect the figure of merit, are additional variables that may be evaluated. [See, e.g., Helmkamp, M. M. & Davis, M. E. Synthesis of porous silicates. Ann. Rev. Mater. *Sci.* 25, 161–192 (1995); and Zones, S. I., Nakagawa, Y., Lee, G. S., Chen, C. Y. & Yuen, L. T. Searching for new high silica zeolites through a synergy of organic templates and novel inorganic conditions. *Micropor. Mesopor. Mat.* 21, 199–211 (1998)].

III. Analogy to Previous Monte Carlo Methods

The combinatorial experiment searches through various values of the variables, e.g., compositional space, to find the one or the few values that result in the best figure of merit. The procedure is analogous to what is done in Monte Carlo simulation, where one searches through configuration space to find configurations with low free energies. We have used an analogy to Monte Carlo algorithm design to find more powerful experimental protocols for combinatorial chemistry searches of compositional space.

The property to be measured in the present invention, i.e., the figure of merit, E, is like the negative of the energy, $-H$, in Monte Carlo searches of configuration space. The temperature, $T=1/\beta$, in previous Monte Carlo methods is like the selection stringency in combinatorial chemistry. One could sample any probability distribution, such as Gaussian, Poisson, or other distributions known to those of skill in the art, in the combinatorial chemistry protocols of the present invention. However, a most preferred distribution is a Boltzmann distribution.

$$\rho \propto \exp(\beta E), \quad (4)$$

which will favor variables associated with low free energies. Another possibility is the Tsallis distribution, $$\rho \propto [1+(1-q)\beta(E-E_0)^{1/(1-q)}]. \quad (5)$$

IV. Preparing a First Set of Samples

In a typical combinatorial chemistry experiment, several samples, e.g., 10,000, are synthesized and screened for their figures of merit at one time. The samples in the first round of the experiment are usually selected by scanning the composition and non-composition variables in a grid-like fashion.

Similarly, the first round of the present method entails preparing a first set of samples, which can include a grid search protocol as in the prior art. However, in other more preferred versions of the present invention, each sample will have at least one variable, and preferably a plurality of composition and non-composition variables, selected by a stochastic method.

Figure 3:
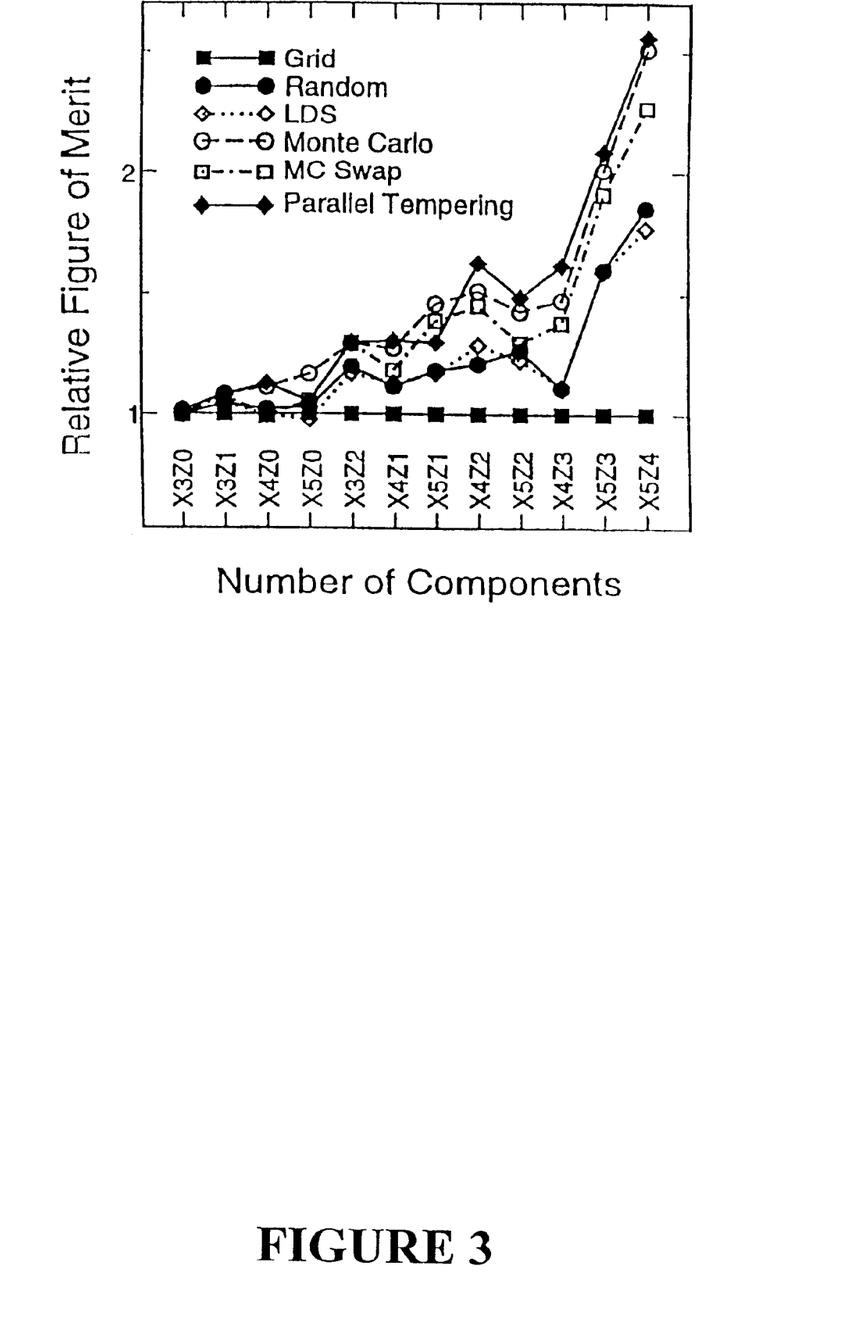
FIG. 3 shows the Monte Carlo methods are especially effective on systems with a larger number of variables, by comparing the maximum figure of merit found with different protocols on systems with different numbers of composition (x) and non-composition (z) variables, scaled to the maximum found by the Grid searching method, wherein each value is averaged over scaled results on 10 different instances of the Random Phase Volume Model with different random tessellations.

More specifically, the first step of a preferred method entails choosing the composition and non-composition variables at random from the allowed values. Alternatively, the variables are selected in a fashion that attempts to maximize the amount of information gained from the limited number of samples screened, via a quasi-random, low-discrepancy sequence [see, e.g., Bratley, P., Fox, B. L. & Niederreiter, H. Algorithm-738-programs to generate Niederreiter's Low-Discrepancy Sequences. *ACM Trans. Math. Software* 20, 494–495 (1994); and Niederreiter, H. Random Number Generation and Quasi-Monte Carlo Methods (Society for Industrial and Applied Mathematics, Philadelphia, 1992); both references incorporated herein in their entirety]. As shown in FIG. 3, which compares the results of various search protocols, such single pass random or LDS searches generally provide higher maximum figures of merit than do similar grid searches.

V. Changing the Variables

With the results of the first round, a new set of samples can be synthesized and screened. This procedure can be repeated for several rounds. In each round, the composition and non-composition variables of each sample from the first round, hereinafter referred to as the current samples, can typically be changed independently, at least in spatially addressable libraries (see, e.g., Pirrung, supra, and Akporiaye et al., supra). The samples of the new set, characterized as having changed variables, shall be referred to hereinafter as proposed samples. Accordingly, the second step of the present invention is preparing a new set of proposed samples by changing the variables of each current sample by a Monte Carlo selection method. Accordingly, the second step of the present invention is preparing a new set of proposed samples by changing the variables of each current sample by a Monte Carlo selection method.

An "internal" and "external" bias can be incorporated into the move. The internal bias must satisfy some normalization condition and can incorporate any a priori knowledge that we have about the system. For example, we can incorporate: (a) likely property values based on a data base, theory, or simulation; (b) cost of raw materials; (c) ease of synthesis; (d) patentability; or (e) other design parameters. The external bias is then determined from a detailed balance formula and aids in making large moves that are likely to be in a fruitful direction.

In one version of the present invention, the variables of the current samples are changed by a random displacement, wherein we randomly change the variables of a randomly chosen current sample a small amount. The characteristic sizes of the random changes in the composition and non-composition variables are parameters that should be optimized. As a rough estimate, for a composition variable (x) expressed as a mole fraction, a small amount for $\Delta x$ would typically be about $0.01/d$ to $0.1/d$, wherein d is the total number of composition variables. A small amount for a non-composition variable would typically be about 5 to 10 percent of the allowed range for that variable. For example, a non-composition variable (z) with an allowed range from $-1$ to 1, would have a $\Delta z$ of about 0.01 to 0.2. These moves are repeated until all the samples in a round have been modified.

In another version of the present invention the second step includes a swapping move, wherein we trade a subset of the variables between at least one pair of randomly chosen samples. This will be most successful in the case where there is a hierarchical structure to the composition space. For example, we might swap the host compositions of two samples, but leave the guest compositions of the samples intact. Alternatively, we might swap the guest compositions instead. In addition, we might swap the impurity composition, temperature, pressure, or processing variables.

Changes that lead to composition values outside the range of allowed values are rejected or the invalid composition value is mapped by reflecting boundary conditions to an allowed value. Preferably, the random displacement of the x variables is done in the d−1 dimensional subspace orthogonal to the d dimensional vector (1, 1, . . . , 1) so that the constraint:

$$\sum_{i=1}^{d} x_i = 1 \quad (6)$$

is maintained. This subspace is identified by the Gram-Schmidt procedure. Moves that violate the constraint $x_i \geq 0$ are rejected. Moves that lead to invalid values of the non-composition variables are also rejected.

VI. Screening the Samples

In the Monte Carlo approach of the present invention, the first round of combinatorial chemistry is initiated with the composition and non-composition variables chosen at random from the allowed values. The variables are changed in succeeding rounds as dictated by the Monte Carlo procedure. We then experimentally measure the values of the figure of merit for the proposed new samples.

The figure of merit can correspond to any experimentally measurable property, such as luminescence, catalytic activity or selectivity, superconductivity, giant or colossal magnetoresistance, dielectric screening, biological activity, binding affinity, or sensing ability. Preferably, such measurements are automated to facilitate the high throughput analysis of multiple samples.

VII. Additional Rounds of Combinatorial Chemistry

Incorporating feedback as the experiment proceeds confers dramatic improvements in search results. An effective way to do this is to treat the combinatorial chemistry experiment as a Monte Carlo in the laboratory, where we decide whether to accept the newly proposed samples or to keep the current samples for the next round according to a Metropolis acceptance criterion. This allows the experimental figure of merit to be sampled in a fashion proportional to $\exp(\beta E)$, where E is the figure of merit we seek to optimize. If $\beta$ is large, then the Monte Carlo procedure will tend to seek out values of the composition and non-composition variables that maximize the figure of merit. If $\beta$ is too large, however, the Monte Carlo procedure will get stuck in relatively low-lying local maxima.

For the random displacement protocol, we decide whether to accept the newly proposed samples or to keep the current samples for the next round according to the Metropolis acceptance criterion:

$$\mathrm{acc}(c \to p) = \min\{1, \exp[\beta(E_{proposed} - E_{current})]\}. \quad (1)$$

Proposed samples that increase the figure of merit are always accepted; proposed samples that decrease the figure of merit are accepted with the Metropolis probability. Allowing the figure of merit occasionally to decrease is what allows samples to escape from local maxima. For the swapping move applied to samples i and j the modified acceptance probability is:

$$\mathrm{acc}(c \to p) = \min\{1, \exp\{\beta[E^i_{proposed} + E^j_{proposed} - E^i_{current} - E^j_{current}]\}. \quad (2)$$

Figure 1:
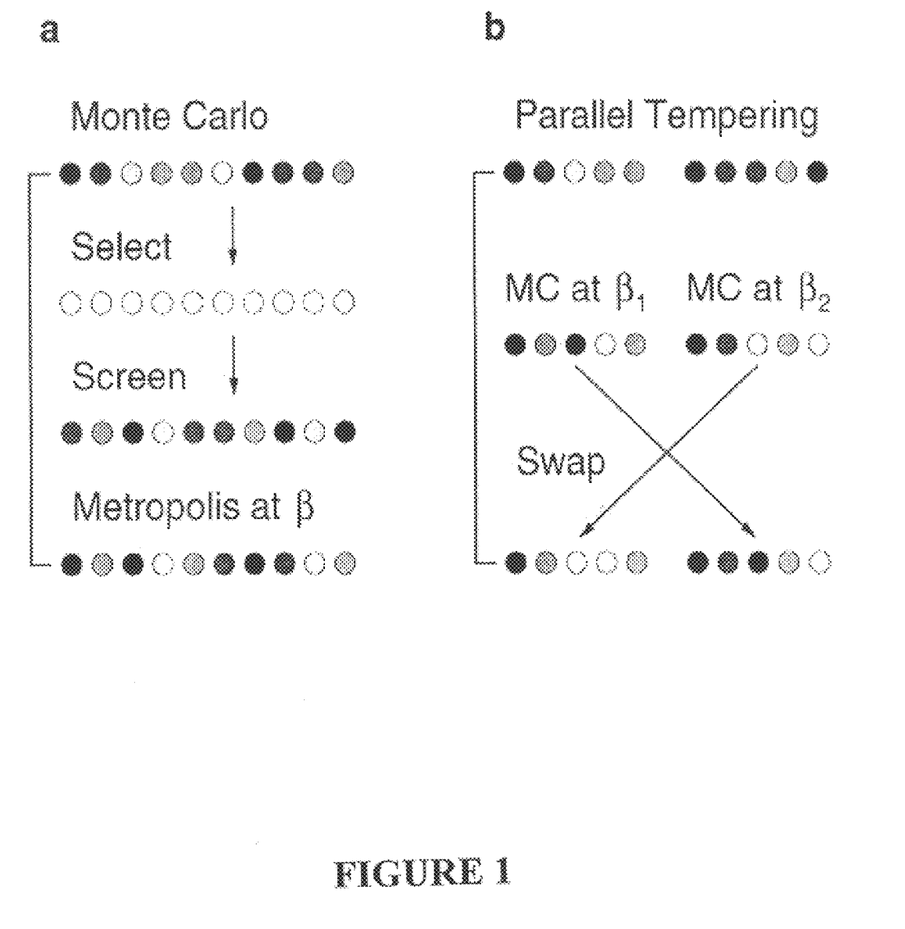
FIG. 1 shows (a) One Monte Carlo round with 10 samples, and (b) One Parallel Tempering round with 5 samples at $\beta_1$ and 5 samples at $\beta_2$.

FIG. 1a shows one round of a Monte Carlo procedure. The parameter $\beta$ used is not related to the thermodynamic temperature of the experiment and simply defines the scale of the variations of the figure of merit that are likely to be accepted. Moreover, the parameter $\beta$ should be optimized for best efficiency.

Preferred versions of the method include additional rounds of combinatorial chemistry, which entail forming a modified set of current samples, changing the variables of the modified set of current samples to form another new set of proposed samples, and screening the new set according to the Metropolis acceptance criterion. The modified set of current samples is formed by comparing the figure of merit of a current sample with that of a proposed sample, wherein the variables of the current sample were changed to give the proposed sample. If the figure of merit of the proposed sample is greater than the figure of merit of the current sample, the proposed sample replaces the current sample in the next round of combinatorial chemistry. The proposed sample replaces the current sample according to a Metropolis probability if the figure of merit of the proposed sample is less than the figure of merit of the current sample.

In another preferred version of the present invention the current samples are first modified by random displacement or swapping. This is done by first going through each of the current samples of the first or modified set. The variables of a current sample can be changed by a simple random displacement, which updates one current sample with a probability, $1-P_{swap}$. Alternatively, the variables of a pair of current samples are changed by a swapping move, with a probability of $P_{swap}$. The random displacement or swapping moves are chosen randomly and the selection process is repeated until all the samples in the subset are updated to give a new set of proposed samples.

If the number of composition and non-composition variables is too great, or if the figure of merit changes with the variables in a too-rough fashion, even normal Monte Carlo will not achieve proper sampling. Another feedback method, parallel tempering, is a more powerful Monte Carlo method that has been used to study statistical, spin glass and molecular systems with rugged energy landscapes. [See, e.g., Geyer, C. J. Markov chain Monte Carlo maximum likelihood in *Computing Science and Statistics: Proceedings of the 23rd Symposium on the Interface* 156–163 (American Statistical Association, New York, 1991; Marinari, E. , Paxisi, G. & Ruiz-Lorenzo, J. Numerical simulations of spin glass systems in Spin Glasses and Random Fields (ed. Young, A.) volume 12 of *Directions in Condensed Matter Physics* (World Scientific, Singapore, 1998); and Falcioni, M. & Deem, M. W. A biased Monte Carlo scheme for zeolite structure solution. *J. Chem. Phys.* 111, 1754–1766 (1999)].

Parallel tempering is our most powerful feedback protocol. In parallel tempering, a first subset of the current samples is updated by Monte Carlo with parameter $\beta_1$, a second subset by Monte Carlo with parameter $\beta_2$, and so on. At the end of each round, samples are randomly exchanged between the subsets with different $\beta$'s, as shown in FIG. 1b. It is important to notice that this extra step does not involve any extra screening compared to Monte Carlo and is, therefore, "free" in terms of experimental costs. This step is, however, dramatically effective at facilitating the protocol to escape from local maxima. The number of different subsets and the $\beta$ values of each subset are parameters that must be optimized.

In a preferred version of the parallel tempering protocol the exchange step is accepted with an acceptance criterion condition.

In a most preferred version of the present invention the current samples are first modified by random displacement or swapping. This is done by first going through each subset. The variables of a current sample can be changed by a simple random displacement, which updates one sample with a probability, $1-P_{swap}$. Alternatively, the variables of a pair of current samples are changed by a swapping move, with a probability of $P_{swap}$. The random displacement or swapping moves are chosen randomly and the selection process is repeated until all the samples in the subset are updated. Then, the entire process is repeated for the next subset. After updating all the subsets to give new subsets of proposed samples, the figures of merit are determined for each sample. The appropriate acceptance criteria are then used to determine which of the proposed samples to accept.

The next step is a parallel tempering procedure that loops through all the subsets, $i=1,2,\ldots n_{subsets}-1$. For example, samples are exchanged, by parallel tempering, between two samples randomly chosen from subsets i and i+1. The total number of samples chosen is generally:

$$2 \times (\text{size of the smaller subset}) \times P_{PT}, \quad (7)$$

wherein $P_{PT} \leq 1$.

Preferably, the Monte Carlo procedures are repeated for several rounds. Typically, at the very end of the protocol, one would perform a deterministic optimization of the most promising lead compounds to find the best local optima of the figure of merit.

We have chosen to sample the figure of merit by Monte Carlo, rather than simply to optimize it globally by some other method, for several reasons. First, Monte Carlo is an effective global optimization method. Second, simple global optimization may be misleading since concerns such as patentability, cost of materials, and ease of synthesis are not usually included in the experimental figure of merit. Moreover, the screen that is most easily performed in the laboratory, the "primary screen", is usually only roughly correlated with the true figure of merit one seeks to optimize. Indeed, after finding materials that look promising based upon the primary screen, experimental secondary and tertiary screens are performed to identify that material which is truly optimal. Third, it might be advantageous to screen for several figures of merit at once. For all these reasons, sampling by Monte Carlo to produce several candidate materials is preferred over global optimization.

VIII. Additional Embodiments

The methods of the present invention can be extended to encompass organic chemistry experiments, where the basic variables are not so much atomic composition, but rather which molecular fragments or substituents are present. Fragments from a fragment library can be added to a given backbone or backbone library. Alternatively, the compound can be built from a series of steps where a chemistry and a fragment are both chosen. In this second case, there is no longer the distinction between backbone and substituent.

In the backbone/substituent case, the basic variables subject to change are the fragments or substituents to add and the backbone itself. As in the solid-state case, both individual changes to the molecules as well as swapping changes can be incorporated into the search protocol. Note that the swapping changes are akin to "DNA Shuffling," where the basic algorithm would be:

1. Change one of the substituents or backbones;
2. Swap two molecules or shuffle molecular fragments;
3. Screen; and
4. Repeat.

The acceptance probabilities are as described above. Note that some of the chemistries to add substituents will fail (maybe 10–20%). This is not a problem, as such incomplete compounds will simply have a low figure of merit. Alternatively, parallel tempering can be used in addition to of the swapping changes in this algorithm.

In another embodiment of the present invention, the organic compounds are built by selecting a series of fragments and chemistries to perform. The variables are the fragments, the chemistries, and the total number of steps. Once the realization that the chemical steps are additional variables is made, this case is like the previous one. Moreover, the variables can be changed as above or sequentially, e.g., first changing fragment 1, then chemistry 1, then fragment 2, then chemistry 2, and so on. In preferred versions, we would assign different probabilities for swapping different fragments. For example, we would probably want to swap the fragments and chemistries near the end of the sequence more often. The method of parallel tempering is an alternative in this case as well.

EXAMPLE 1

Figure 2:
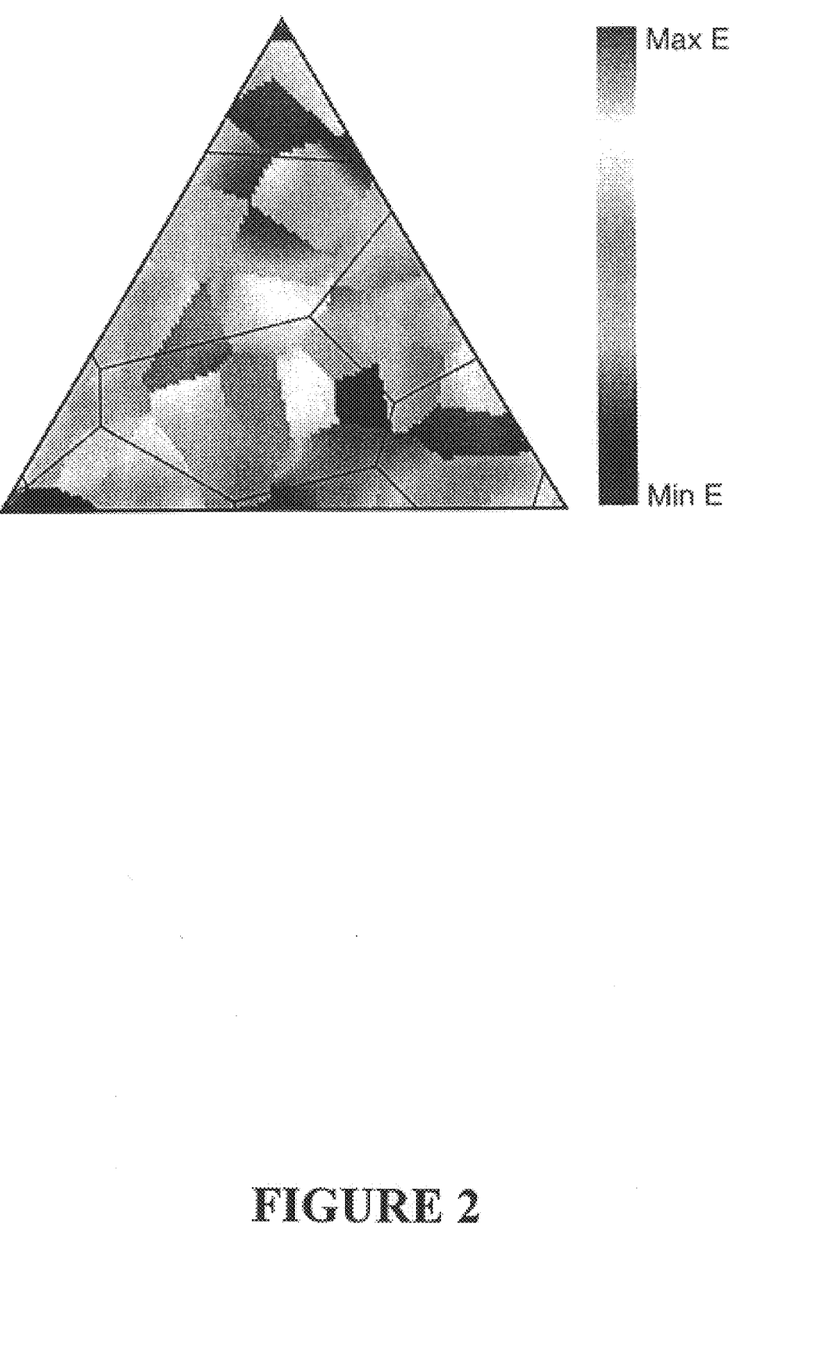
FIG. 2 shows the Random Phase Volume Model for the case X3Z1, where the boundaries of the x phases are evident by the sharp discontinuities in the figure of merit, the z variable was held constant and the boundaries of the z phases are shown as thin dark lines.

We demonstrate the effectiveness of these protocols by combinatorial chemistry experiments as simulated by the Random Phase Volume Model. This model relates the figure of merit to the composition and non-composition variables in a statistical way. The model is fast enough to allow for validation of the proposed searching methods on an enormous number of samples, yet possesses the correct statistics for the figure-of-merit landscape. We denote the d-dimensional vector of composition mole fractions by x. We group the composition variables into phases defined by a Voronoi tessellation of $N_x$ points $x_\alpha$ randomly placed within the simplex of allowed compositions (see FIG. 2). The model is defined for any number of composition variables, and the number of phase points is defined by requiring the average spacing between phase points to be $\xi = 0.25$. To avoid edge effects, we add additional points in a belt of width $2\xi$ around the allowed simplex. Physically, we expect the figure of merit to change dramatically between composition phases. Moreover, within each phase $\alpha$, the figure of merit should also vary with $y = x - x_\alpha$, due to crystallinity effects such as crystallite size, intergrowths, defects, and faulting (van Dover et al., supra). In addition, the non-composition variables should also affect the measured figure of merit. The non-composition variables are denoted by the b-dimensional vector z, with each component constrained to fall within the range [−1, 1] without loss of generality. There can be any number of non-composition variables, which also fall within $N_z$ "z-phases" defined in the space of composition variables. There are a factor of 10 fewer non-composition phases than composition phases. The functional form of the model when x is in composition phase $\alpha$ and z-phase $\gamma$ is $$E(x, z) = U_a + \sigma_x \sum_{k=1}^{q} \sum_{r_1 \geq \ldots \geq a=1}^{d} f_{i_1 \ldots i_k} \xi_x^{-k} A_{i_1 \ldots i_1}^{\alpha k} y_{i_1} y_{i_1} \ldots y_{i_1} + \tag{8}$$

$$1/2 \left( W_v + \sigma_z \sum_{k=1}^{a} \sum_{r_1 \geq \ldots \geq a=1}^{b} f_{i_1 \ldots i_k} \xi_z^{-k} B_{i_1 \ldots i_1}^{\gamma k} z_{i_1} z_{i_1} \ldots z_{i_1} \right)$$

where $f_{i_1 \ldots i_k}$ is a constant symmetry factor, and $U_a$, $W_a$, $A_{i_1 \ldots i_k}^{\alpha k}$ and $B_{i_1 \ldots i_k}^{\gamma k}$ are random Gaussian variables with unit variance. In more detail, the symmetry factor is given by:

$$f_{i_1 \ldots i_k} = \frac{k!}{\prod_{i=1}^{l} o_i!} \tag{9}$$

where L is the number of distinct integer values in the set $\{i_1, \ldots, i_k\}$, and $o_i$ is the number of times that distinct value i is repeated in the set. Note that $1 \leq I \leq k$ and $$\sum_{i=1}^{l} o_i = k \tag{10}$$

The scale factors are chosen so that each term in the multinomial contributes roughly the same amount: $\xi_x = \xi/2$ and $\xi_z = [(z^6)/(z^2)]^{1/4} = (\frac{3}{7})^{1/4}$. The $\sigma_x$ and $\sigma_z$ are chosen so that the multinomial crystallinity terms contribute 40% as much as the constant phase terms on average. We choose q=6 for both multinomials. As FIG. 2 shows, the Random Phase Volume Model describes a rugged figure of merit landscape, with subtle variations, local maxima, and discontinuous boundaries.

We demonstrate six different search protocols with increasing numbers of composition and non-composition variables, varying d from 3 to 6 and b from 0 to d−1. We scaled the number phases, $N_x$, so as to maintain the average phase size $\xi = 0.25$ constant. We fixed the total number of samples whose figure of merit will be measured at M=100,000, so that all protocols have the same experimental cost.

First, we considered three single pass protocols: Grid, Random, and LDS. For the Grid method, we defined $M_x = M^{(d-1)/(d-1+b)}$ and $M_z = M^{b/(d-1+b)}$. The grid spacing of the composition variables, $\zeta_x$, was determined according to $\zeta_x = (M_x/V_d)^{1/(d-1)}$, where:

$$V_d = \frac{\sqrt{d}}{d-1!} \quad (11)$$

is the volume of the allowed composition simplex. The spacing for each component of the non-composition variables is $\zeta_z = M_z^{1/b}/2$. For the LDS method, we used different quasi-random sequences for the composition and noncomposition variables.

We also considered three feedback protocols: Monte Carlo, Monte Carlo with swap, and Parallel Tempering. We optimized the Monte Carlo parameters on test cases, finding it optimal to perform 100 rounds of 1,000 samples and to use $\beta=2$ when $d=3$, $\beta=1$ when $d=4$ or 5; $\Delta x=0.1/d$; and $\Delta z=0.12$ for the maximum random displacement in each component. For the Monte Carlo with swap we used $P_{swap}=0.1$ for the probability of a swap versus a regular random displacement. For Parallel Tempering it was optimal to perform 100 rounds with 1,000 samples, divided into three subsets: 50 samples at $\beta=50$, 500 samples at $\beta=10$, and 450 samples at $\beta=1$. The 50 samples at large $\beta$ essentially perform a "steepest-ascent" optimization and have smaller $\Delta x=0.01/R_d$ and $\Delta z=0.012$.

The results of the runs are shown in FIG. 3. It is clear that Random and LDS protocols find better solutions than does Grid in one round of experiment. More importantly, the Monte Carlo feedback methods have a tremendous advantage over one pass methods, especially as the number of variables increases, with Parallel Tempering the best method. Note that in cases such as catalytic activity, sensor response, or ligand specificity, the experimental figure of merit would likely be exponential in the values shown in FIG. 3, so that the success of the Monte Carlo methods would be even more dramatic. A better calibration of the parameters in Eq. 1 may be possible as more data becomes available in the literature.

EXAMPLE 2

The following proof-of-principal experiment demonstrates a practical engineering application of the combinatorial chemistry invention described herein. Catalysis of the oxidation reaction:

$$CH_3OH + H_2O \rightarrow CO_2 + 6H^+ + 6e^-, \quad (12)$$

is important in the context of direct methanol fuel cells (DFMC) (Reddington et al., supra). Since methanol is a renewable liquid fuel, DMFCs have some advantages over traditional combustion engines and hydrogen fuel cells for vehicular transport and remote power applications. DMFCs are non-polluting and use a high-energy-density, easily-distributed fuel [Fuller, T. F., *Electrochem. Soc. Interface,* 144, 1543, (1997)]. Unfortunately, current anode and cathode electrocatalysts produce significant current densities only at high voltage over potentials, which is undesirable. The anode catalyst, which catalyzes reaction 2 above, is particularly limiting.

Catalysts for this reaction have been identified by a brute force combinatorial search of five component mixtures of Pt, Ru, Os, Ir, and Rh (Reddington et al., supra). Only four components could be searched at a time due to the difficulty of performing a grid search in this high-dimensional space. Even so, a catalyst significantly better than the previous best catalyst, discovered after 30 years of laborious work, was identified.

A search like this for improved catalysts is a good test system for our novel approach to combinatorial chemistry. The space of variables is large enough that grid searching is just barely adequate, so the methods of the present invention should perform better. Yet, the space of variables is simple enough that there are previous results in Reddington et al, supra, for purposes of comparison.

The experimental methodology for this system is relatively straightforward. Detection of catalytic products is especially simple, since the ion imbalance generated by the reaction can be seen by emission of a fluorescent indicator dye. Following the strategy of Reddington et al., supra, the reactants are first be prepared as aqueous inks from $H_2PtCl_6 \cdot H_2O$, $RuCl_3 \cdot xH_2O$, $OsCl_3$, $K_2IrCl_6$, and $RhCl_3 \cdot 2.4H_2O$, which are then diluted to the required viscosity by the addition of glycerol. The reactants are then dispensed with a modified commercial ink-jet printer. Samples are "printed" onto a page and then reduced with a borohydride reduction. The samples are then dried, washed, and subjected to electric over-potentials in a methanol solution. Reaction products are identifiable by a color change of a fluorescent indicator dye, such as quinine or the $Ni^{+2}$ complex of 3-pyridin-2-yl-<4,5,6>triazolo-<1,5-a>pyridine (PTP). Detection can be by a fluorescent microscope or a modified commercial flat-bed scanner.

Implementation of the control algorithm simply requires replacing the figure of merit returned by the Random Phase. Volume Model with the experimental figure of merit measured by the flat bed scanner. The 1,000 or so required samples are printed on one "page," and the 100 or so "pages" produced by the 100 rounds of combinatorial chemistry are scanned. As will be apparent to those of skill in the art, automatic controls of the ink-jet printer and scanner are simply accomplished via existing printer and scanner drivers.

Proof of principle experiments are carried out using this combinatorial system for discovery of catalysts for direct conversion of methanol. For purposes of comparison, the conventional combinatorial chemistry of Reddington et al., supra, has identified a particularly good 4-component catalyst. Since 4-component systems are the upper limit of complexity that such conventional chemistry can handle, repeating this experiment with 4- and 5-component catalyst mixtures demonstrates the effectiveness of the proposed methods.

The experimental challenges in combinatorial chemistry appear to lie mainly in the technology for the creation of the libraries and the screening methods. The theoretical challenges, on the other hand, appear to lie in the library design and redesign. We have addressed this second question via an analogy between combinatorial materials discovery and Monte Carlo computer simulation. The protocols developed with this approach are substantially superior to current methods, especially on systems with larger numbers of composition and non-composition variables. These protocols, when combined with appropriate robotic controls, should allow the practical application of combinatorial chemistry to more complex and interesting systems.

Although the present invention has been described in considerable detail with reference to certain preferred versions thereof, other versions are possible. For example, one could do the updating of samples by random displacement, swapping, and parallel tempering in a different sequence than the preferred versions disclosed herein. In addition, one could use other Markov chain Monte Carlo protocols in addition to Metropolis, swapping, and parallel tempering. Moreover, these methods could be applied to biological combinatorial chemistry, e.g., protein molecular evolution. Therefore, the spirit and scope of the appended claims should not be limited to the description of the preferred versions contained herein.

What is claimed is:

1. A method for generating a combinatorial library, comprising:
   (a) preparing a first set of current samples, each current sample comprising a composition having two or more variables, wherein said variables are composition or non-composition variables, each variable having a value;
   (b) preparing a new set of proposed samples by changing the values of the variables of each current sample by a Monte Carlo selection method, wherein the values of the variables are randomly changed a small amount;
   (c) experimentally measuring a figure of merit for each current and proposed sample; and
   (d) forming a modified set of current samples according to an acceptance criterion comprising a detailed balance probability, wherein the detailed balance probability includes a Metropolis probability, whereby:
      (1) a proposed sample replaces a current sample, wherein the values of the variables of the current sample were changed to give the proposed sample, if the figure of merit of the proposed sample is greater than the figure of merit of the current sample, and
      (2) if the figure of merit of the proposed sample is less than the figure of merit of the current sample, the proposed sample is accepted according to a Metropolis probability, the Metropolis probability being determined by the formula:

$$p=\min\{1, \exp[\beta(E_{proposed}-E_{current})]\}, \quad (1)$$

wherein $\beta$ is an empirically determined parameter that defines a scale for variations of the figure of merit that are likely to be accepted, $E_{proposed}$ is the figure of merit of the proposed sample and $E_{current}$ is the figure of merit of the current sample.

2. The method of claim 1, wherein the sets of samples comprise two or more subsets, each subset forming a modified subset of current samples as in (d), each subset being updated with a different detailed balance probability having a different empirically determined parameter $\beta$, which defines a scale for variations of the figure of merit that are likely to be accepted, with the additional step of randomly exchanging two or more samples, by parallel tempering, between the subsets.

3. The method of claim 1, further comprising:
   (e) repeating steps (b) through (d) for one or more rounds until a maximum figure of merit is obtained.

4. The method of claim 1, wherein the composition variables are one or more mole fractions of an element or compound.

5. The method of claim 1, wherein the non-composition variables include the chemistries to perform at each step and the total number of steps.

6. The method of claim 1, wherein the non-composition variables are selected from the group consisting of film thickness, deposition method, guest composition, host composition, impurity level, temperature, pressure, pH, atmospheric composition, crystallinity, phase, morphology, method of nucleation, and method of synthesis.

7. The method of claim 1, wherein the composition variables are mole fractions, $x_i$, for one or more elements, i, from 1 to d, wherein the allowed values for the $x_i$ are equal to or greater than 0 and the sum of all the $x_i$ for elements i from 1 to d is equal to 1.

8. The method of claim 1, wherein the non-composition variable is pressure and the allowed values are about 0 to about 100 atmospheres.

9. The method of claim 1, wherein the non-composition variable is temperature and the allowed values are about 0 K to about 4,000 K.

10. The method of claim 1, wherein the non-composition variable is thickness and the allowed values are about 0 to about 1 mm.

11. The method of claim 1, wherein the figure of merit measures a property selected from the group consisting of luminescence, catalytic activity or selectivity, superconductivity, giant or colossal magnetoresistance, dielectric screening, biological activity, binding affinity, or sensing ability.

12. A method for generating a combinatorial library, comprising:
   (a) preparing a first set of current samples, each current sample comprising a composition or a molecule having two or more variables, each variable having a value;
   (b) preparing a new set of proposed samples by changing the values of the variables of the current samples by a Monte Carlo selection method, which includes at least one swapping step, wherein the values of a subset of variables is traded between two current samples, i and j, to give two proposed samples, i and j;
   (c) experimentally measuring a figure of merit for each current and proposed sample; and
   (d) forming a modified set of current samples according to an acceptance criterion comprising a detailed balance probability, wherein the detailed balance probability of accepting the proposed samples of the swapping step is determined by the formula:

$$p=\min\{1, \exp\{\beta[E^i_{proposed}+E^j_{proposed}-E^i_{current}-E^j_{current}]\}, \quad (2)$$

wherein the empirically determined parameter $\beta$ defines the scale of the variations of the figure of merit that are likely to be accepted, $E^i_{proposed}$ is the figure of merit of the proposed sample i, $E^j_{proposed}$ is the figure of merit of the proposed sample j, $E^i_{current}$ is the figure of merit of the current sample i and $E^j_{current}$ is the figure of merit of the current sample j.

13. The method of claim 12, wherein the variable is a backbone, fragment or substituent.

14. A method for generating a combinatorial library, comprising:
   (a) preparing a first set of current samples, each current sample comprising a composition having two or more variables, wherein said variables are composition or non-composition variables, each variable having a value; and
   (b) preparing a new set of proposed samples by changing the values of the variables of each current sample by a Monte Carlo selection method, wherein the variables are changed by:
      (1) randomly changing the value of at least one of the composition and non-composition variables of a randomly chosen current sample a small amount; and
      (2) swapping the values of a subset of the variables between at least one pair of randomly chosen current samples.

15. The method of claim 14, which includes at least one swapping step, wherein the values of a subset of variables is are traded between two current samples, i and j, to give two proposed samples, i and j, and the detailed balance probability of accepting the proposed samples of a swapping step is determined by the formula:

$$p=\min\{1, \exp\{\beta[E^i_{proposed}+E^j_{proposed}-E^i_{current}-E^j_{current}]\}, \quad (2)$$

wherein $\beta$ is an empirically determined parameter that defines a scale for variations of the figure of merit that are likely to be accepted, $E^i_{proposed}$ is the figure of merit of the proposed sample i, $E^j_{proposed}$ is the figure of merit of the proposed sample j, $E^i_{current}$ is the figure of merit of the current sample i and $E^j_{current}$ is the figure of merit of the current sample j.

16. A method for generating a combinatorial library, comprising:
  (a) preparing a first set of current samples, each set of samples comprising two or more subsets, each current sample comprising a composition or a molecule having two or more variables that can be changed independently, each variable having a value;
  (b) preparing a new set of proposed samples by changing the values of the variables of each cent sample by a Monte Carlo selection method;
  (c) experimentally measuring a figure of merit for each current and proposed sample;
  (d) forming a modified set of current samples, each subset forming a modified subset of current samples, each subset being updated with a different detailed balance probability having a different empirically determined parameter $\beta$; which defines the scale of the variations of the figure of merit that are likely to be accepted, and
  (e) randomly exchanging two or more samples, by parallel tempering, between the subsets, wherein the exchange of two samples by parallel tempering is accepted according to an acceptance criterion derived from a detailed balance condition.

17. The method of claim 16, wherein the variable is a backbone, fragment or substituent.

* * * * *